(12) United States Patent
Northey

(10) Patent No.: US 8,784,900 B2
(45) Date of Patent: Jul. 22, 2014

(54) ANTIMICROBIAL SOLUTIONS CONTAINING DICHLORINE MONOXIDE AND METHODS OF MAKING AND USING THE SAME

(75) Inventor: Robert Northey, Bellevue, WA (US)

(73) Assignee: Oculus Innovative Sciences, Inc., Petaluma, CA (US)

( * ) Notice: Subject to any disclaimer, the term of this patent is extended or adjusted under 35 U.S.C. 154(b) by 445 days.

(21) Appl. No.: 12/531,276

(22) PCT Filed: Mar. 13, 2008

(86) PCT No.: PCT/US2008/056919
§ 371 (c)(1),
(2), (4) Date: Jan. 20, 2010

(87) PCT Pub. No.: WO2008/112940
PCT Pub. Date: Sep. 18, 2008

(65) Prior Publication Data
US 2010/0112092 A1 May 6, 2010

Related U.S. Application Data

(60) Provisional application No. 60/906,939, filed on Mar. 13, 2007.

(51) Int. Cl.
| | | |
|---|---|---|
| A01N 59/00 | (2006.01) | |
| A61K 33/08 | (2006.01) | |
| A01N 25/04 | (2006.01) | |
| A01N 31/02 | (2006.01) | |
| C01B 7/03 | (2006.01) | |
| C01B 11/02 | (2006.01) | |
| B01J 19/00 | (2006.01) | |
| B01J 31/02 | (2006.01) | |

(52) U.S. Cl.
USPC .......... 424/661; 424/405; 424/422; 424/427; 424/434; 424/435; 424/436; 424/437; 423/210; 423/462; 423/497; 423/499.1; 423/500; 252/181.4; 252/181.7

(58) Field of Classification Search
USPC ......... 424/661, 405, 422, 427, 434, 435, 436, 424/437; 423/210, 462, 497, 499.1, 500; 252/181.4, 181.7
See application file for complete search history.

(56) References Cited

U.S. PATENT DOCUMENTS 4,146,578 A * 3/1979 Brennan et al. ............... 423/473
4,190,638 A * 2/1980 Hoekje et al. ................. 423/473
(Continued)

FOREIGN PATENT DOCUMENTS

CN 1487835 A 4/2004
DE 30 46 324 A1 12/1982
(Continued)

OTHER PUBLICATIONS http://en.wikipedia.org/wiki/Buffer_solution (1921-2000).*
(Continued)

Primary Examiner — Jane C Oswecki
(74) Attorney, Agent, or Firm — Leydig, Voit & Mayer, Ltd.

(57) ABSTRACT

Methods and products are provided for treating a wound or infection in a mammal or disinfecting a surface with a hypochlorous acid solution that has been activated by a catalyst. Additionally provided is a process for preparing an antimicrobial product that produces an activated hypochlorous acid solution for use as an antimicrobial.

30 Claims, 5 Drawing Sheets

(56) References Cited

U.S. PATENT DOCUMENTS

| | | | |
|---|---|---|---|
| 5,037,627 A * | 8/1991 | Melton et al. ................. | 423/473 |
| 5,152,915 A * | 10/1992 | Ralston et al. ............ | 252/186.36 |
| 5,888,528 A * | 3/1999 | Wellinghoff et al. ......... | 424/405 |
| 7,758,807 B2 * | 7/2010 | Smith et al. ..................... | 422/37 |
| 2004/0062818 A1 * | 4/2004 | Calderon ..................... | 424/661 |
| 2004/0226894 A1 * | 11/2004 | Okazaki ....................... | 210/756 |
| 2005/0113276 A1 | 5/2005 | Taylor et al. | |

FOREIGN PATENT DOCUMENTS

| | | |
|---|---|---|
| JP | 2005-507395 A | 3/2005 |
| JP | 2007-512356 A | 5/2007 |
| JP | 2007-522222 A | 8/2007 |
| JP | 2007-523137 A | 8/2007 |
| JP | 2008-530022 A | 8/2008 |
| RO | 117 540 B1 | 4/2002 |
| WO | 2005/051342 A1 | 6/2005 |
| WO | 2005/077056 A2 | 6/2005 |
| WO | 2005/079745 A2 | 9/2005 |
| WO | 2006/084251 A2 | 8/2006 |

OTHER PUBLICATIONS http://www.cff.org/AboutCF/index.cfm?dspPrintReady=Y (1955).*
"Buffer solution", Wikipedia [online], [retrieved Sep. 16, 2011] Retrieved from the Internet: <URL: http://en.wikipedia.org/wiki/Buffer_solution>.*
"Cystic Fibrosis Treatments", Cystic Fibrosis Foundation [online], [retrieved Jun. 28, 2012] Retrieved from the Internet: <URL: http://cystic-fibrosis.emedtv.com/cystic-fibrosis/treatment-for-cystic-fibrosis.html> (Not provided; previously supplied).*
W.A. Prutz, "Reactions of Hypochlorous Acid with Biological Substrates are Activated Catalytically by Tertiary Amines," 1998, Arch. Biochem. and Biophysics, 357(2):265-273.*
"Buffer solution", Wikipedia [online], [retrieved Sep. 16, 2011] Retrieved from the Internet: <URL: http://en.wikipedia.org/wiki/Buffer-_solution>.*
"Cystic Fibrosis Treatments", Cystic Fibrosis Foundation [online], [retrieved Jun. 28, 2012] Retrieved from the Internet: <URL: http://cystic-fibrosis.emedtv.com/cystic-fibrosis/treatment-for-cystic-fibrosis.html>.*
International Preliminary Report on Patentability issued in PCT/US2008/056919, dated Sep. 15, 2009.
Bunyan, *J. Trop. Pediatr.*, "The Treatment of Burns by Hypochlorite Solution," 29(2):93-94 (1983).
Prutz, *Arch. Biochem. Biophys.*, "Reactions of Hypochlorous Acid with Biological Substrates are Activated Catalytically by Tertiary Amines," 357(2):265-273 (1998).
European Patent Office, International Search Report in International Application No. PCT/US2008/056919 (Jul. 23, 2009).

* cited by examiner

ANTIMICROBIAL SOLUTIONS CONTAINING DICHLORINE MONOXIDE AND METHODS OF MAKING AND USING THE SAME

CROSS-REFERENCE TO RELATED APPLICATIONS

This application is a national stage entry of International Patent Application No. PCT/US08/56919 under 35 U.S.C. §371, filed Mar. 13, 2008, which claims priority to U.S. Provisional Application 60/906,939, filed Mar. 13, 2007, each of which is incorporated herein in its entirety.

BACKGROUND OF THE INVENTION

Skin ulcers are a significant clinical problem and can cause even more serious complications such as, for example, gangrene, systemic inflammatory syndrome, and sepsis. When these complications occur in skin ulcers on the extremities current treatment regimens may require amputations including above-the-knee leg amputation (AKA), below-the-knee leg amputations (BKA), and digital amputations with their obvious implications for the patient.

Skin ulcers have many causes, including venous insufficiency, arterial insufficiency, ischemic pressure, and neuropathies. Venous skin ulcers are the most common type of leg skin ulcers with women affected more than men. Venous skin ulcers are associated with venous hypertension and varicosities. Arterial skin ulcers are typically found in elderly patients with history of cardiac or cerebrovascular disease, leg claudication, impotence, and pain in distal foot. Pressure skin ulcers result from tissue ischemia. Pressure skin ulcers are commonly deep and often located over bony prominences. Neuropathic skin ulcers are associated with trauma, prolonged pressure, usually plantar aspect of feet in patients with, for example, diabetes, neurologic disorders or Leprosy.

Diabetes is also a frequent cause of foot skin ulcers. Diabetes is highly prevalent in the U.S. In addition, type-2 diabetes appears to be increasing in the U.S. Diabetes is the leading nontraumatic cause of amputation in the U.S. The total number of lower-extremity amputations (LEAs) in diabetic patients in the U.S. is over 80,000 annually. The 3-year mortality rate after a diabetic LEA is between 35 and 50%. Direct medical costs for diabetic LEAs in the U.S. are exceptionally high. Foot skin ulcers precede about 85% of LEAs in patients with diabetes. The 1-year incidence of new foot skin ulcers in patients with diabetes in the U.S. ranges from 1.0 to 2.6%. V. R. Driver et al., Diabetes Care 2005 28:248-253.

Work-related burns are a leading cause of acute occupational injury in the U.S. An estimated 20-30% of all hospitalizations due to burn injuries result from workplace exposures. The injuries cause substantial direct costs and resulted in significant loss of productivity.

Peritonitis is an inflammation of the internal lining of the abdominal cavity. The most common causes of peritonitis are bacterial infection and chemical irritation. Bacterial peritonitis is usually secondary to bacterial penetration through an abdominal organ as occurs with disorders such as appendicitis, acute cholecystitis, peptic ulcers, diverticulitis, bowel obstruction, pancreatitis, mesenteric thrombosis, pelvic inflammatory disease, tumor or penetrating trauma, or combinations thereof. In addition, spontaneous bacterial peritonitis (SBP) can develop without an obvious source of contamination. SBP is frequently associated with immunosuppressed states, such as cirrhotic ascites or the nephrotic syndrome. Peritonitis is also a common complication of chronic ambulatory peritoneal dialysis (CAPD).

Periodontal (gum) diseases, including gingivitis and periodontitis, are serious infections that if left untreated, can lead to tooth loss. Periodontal disease can affect one tooth or many teeth. Periodontal disease begins when the bacteria in "plaque," a sticky, colorless film that constantly forms on teeth, causes the gums to become inflamed. In the mildest film of the disease, gingivitis, the gums redden, swell and bleed easily. Gingivitis is often caused by inadequate oral hygiene. Gingivitis is reversible with professional treatment and good oral home care.

However, untreated gingivitis can advance to periodontitis. With time, plaque can spread and grow below the gum line. Toxins produced by the bacteria in plaque irritate the gums. Gums can then separate from the teeth, forming spaces between the teeth and gums that become infected. As the disease progresses, gum tissue and bone are destroyed. Eventually, teeth can become loose and may have to be removed by periodontal surgery.

In addition, root canal infection, an infectious disease of bacterial etiology, is an important cause of tooth loss in the world. Current therapeutic modalities include scaling and root planning of the surfaces of the teeth to eliminate bacterial plaque and calculus, and the use of antiseptic solutions to combat the infectious process caused by a wide spectrum of oral micro-organisms. These antiseptics, however, have high toxicity and consequently cannot be used for prolonged periods. Unfortunately, some of the commonly used antiseptics have adverse side effects such as distortion of taste and staining of teeth.

Non-toxic disinfectants are used to eradicate microorganisms, including bacteria, viruses and spores, in variety of settings. For example, such disinfectants find application in wound care, medical device sterilization, food sterilization, hospitals, consumer households and anti-bioterrorism.

Oxidative-reductive potential ("ORP") water solutions provide highly effective, yet non-toxic treatments for the foregoing condition, as well as other medical conditions. Further, ORP water solutions are effective disinfectants. Known ORP water solutions, however, require rather costly electrolytic manufacturing processes to produce, and also have stability and shelf life problems. There is a need for an ORP water product, which is non-toxic and effective for treating wounds and other medical conditions (e.g., infections), and yet relatively inexpensive to manufacture and has improved shelf life. The present invention provides such an ORP water product, and methods of making and using such a product.

BRIEF SUMMARY OF THE INVENTION

The invention provides methods for treating a wound or infection in a mammal, the methods comprising adding to a solution comprising an effective amount of hypochlorous acid a catalyst, which catalyzes the conversion of hypochlorous acid into dichlorine monoxide, to produce an activated solution comprising a therapeutically effective amount of dichlorine monoxide, and administering the activated solution to treat the wound or infection.

The invention also provides methods for disinfecting a surface, the methods comprising adding to a solution comprising an effective amount of hypochlorous acid a catalyst, which catalyzes the conversion of hypochlorous acid into dichlorine monoxide, to produce an activated solution comprising a surface-disinfecting effective amount of dichlorine monoxide, and contacting the surface with the activated solution to disinfect the surface.

The invention additionally provides products for treating a wound or infection, the products comprising a first component comprising an effective amount of a hypochlorous acid solution, and a second component comprising a catalyst, which catalyzes the conversion of hypochlorous acid into dichlorine monoxide, wherein the first and second components produces when combined produce an activated solution comprising a therapeutically effective amount of dichlorine monoxide.

The invention further provides products for disinfecting a surface, the products comprising a first component comprising an effective amount of a hypochlorous acid solution, and a second component comprising a catalyst, which catalyzes the conversion of hypochlorous acid into dichlorine monoxide, wherein the first and second components when combined produce an activated solution comprising a surface-disinfecting effective amount of dichlorine monoxide.

The products of the invention can further include instructions for combining the first and second components to produce the activated solution, and treating a wound or infection or disinfecting a surface with the activated solution.

In yet other embodiments, the invention provides processes for preparing an antimicrobial product comprising a first container and a second container, the process comprising:
preparing a solution comprising an effective amount of hypochlorous acid;
containing the hypochlorous acid solution within the first container; and
containing in a second container a catalyst, which catalyzes the conversion of hypochlorous acid into dichlorine monoxide,
wherein when the hypochlorous acid solution and catalyst are combined, the combination produces an activated solution comprising a antimicrobially effective amount of dichlorine monoxide.

The methods, products and processes of the invention include embodiments wherein the hypochlorous acid solution comprises a buffer, such as, e.g., a phosphate buffer, acetate buffer, citrate buffer, borate buffer or a combination thereof.

Accordingly, the hypochlorous acid solution has a pH of from about 5.0 to about 6.0. In other embodiments, wherein the activated solution has a pH of from about 5.0 to about 6.0.

The catalyst can include, e.g., a phosphate ion, chloride ion, tertiary amine, sodium hypochlorite, and citric acid or a combination thereof. In some embodiments the catalyst is triethanolamine. In particularly preferred embodiments the triethanolamine is present in a concentration of about 0.3 ppm to about 1.5 ppm.

The methods, products and processes of the invention can treat an infection caused by a bacterium, a virus, a yeast or a combination thereof, including wherein the infection is a pulmonary, ophthalmic, otic, nasal or sinus infection. Suitable wounds for treatment with the invention include, for example, oral ulcers, skin ulcers, burns, peritonitis, periodontal diseases, gingival diseases or a combination thereof. Suitable skin ulcers include diabetic foot ulcers and treatable forms of peritonitis include infectious peritonitis.

The hypochlorous acid solution can be made, e.g., by dissolving chlorine in a dilute aqueous alkali metal hydroxide solution or by electrolysis.

DETAILED DESCRIPTION OF THE INVENTION

Figure 1:
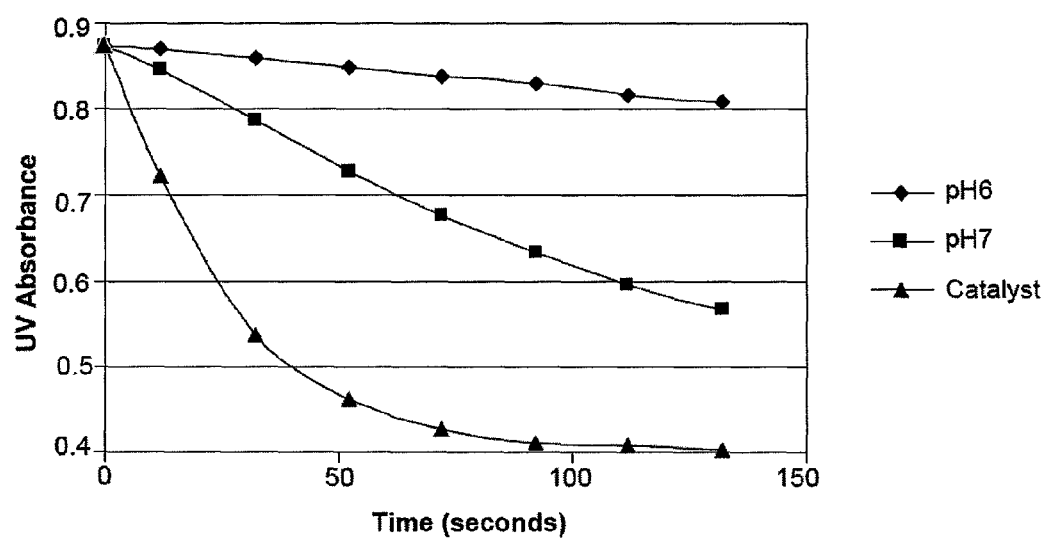
FIG. 1. UV absorption of the solution at 250 nm is measured over a 2 minute period under different conditions showing the consumption of 4-hydroxy benzoic acid by dichlorine monoxide generated in the cuvette.

By "hypochlorous acid solution" it is meant an aqueous solution comprising hypochlorous acid and dichlorine monoxide in chemical equilibrium, including, e.g., hypochlorous acid solutions wherein the rate of conversion of hypochlorous acid to dichlorine monoxide is held at a minimum by exclusion of rate increasing salts. By an "activated solution" or an "activated hypochlorous acid solution" it is meant the hypochlorous acid solution after the catalysts is added.

One skilled in the art will appreciate that suitable methods of administering the activated hypochlorous acid solution of the present invention are available, and, although more than one route of administration can be used, a particular route can provide a more immediate and more effective reaction than another route. The "effective amount" can be the amount necessary to achieve an "effective level" of the activated hypochlorous acid solution in an individual patient. The "effective amount" can be defined, for example, as the amount required to be administered to an individual patient to achieve a blood level, tissue level, and/or intracellular level of the ORP water of the present invention to prevent or treat the condition in the patient. It will be appreciated that an effective amount can include a "therapeutically effective amount." A "surface-disinfecting effective amount" is a degree of disinfection suitable for the intended use of the surface.

By "treating" a disease or condition it is meant attempting to cure of the disease or ameliorate or reducing the morbidity caused by the disease or condition to an acceptable level. By "preventing" a disease or condition it is meant reducing the incidence of likelihood of the disease or condition by a statistically significant amount, such as e.g., reducing the incidence by 5%, 10%, 20%, 30%, 33%, 50%, 67%, 90% or more.

Oxidative-reductive potential (ORP) water solutions typically contain hypochlorous acid (HOCl), which is in equilibrium with minute amounts of dichlorine monoxide in aqueous solution:

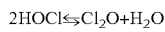

$$2HOCl \leftrightarrows Cl_2O + H_2O$$

In a very dilute solution of HOCl in water at pH=6, the amount of $Cl_2O$ present is very low due to the large excess of water that shifts the equilibrium away from $Cl_2O$. The invention provides for catalysts that shift the equilibrium somewhat toward $Cl_2O$ even in dilute solutions. Several catalysts of different strengths have been identified, including for example, chloride ($Cl^-$) and hypochlorite ($OCl^-$). Salts of $Cl^-$ and $OCl^-$ are also useful as a catalyst including, for example, the sodium, potassium and calcium salts.

In addition, the invention provides for the use of other catalysts including, for example, triethanolamine (TEA) which generates high rates of conversion to $Cl_2O$ at addition levels as low as 1 ppb. The amount of catalyst present in the antimicrobial solution depends on the properties of the catalyst. Generally, catalysts are present in an amount of at least 1 ppb. After the catalyst is added the ORP water solution becomes "activated," i.e., it rapidly generates $Cl_2O$.

In one aspect, the invention provides an antimicrobial solution equilibrium that is active against bacteria, viruses or yeasts. This solution includes hypochlorous acid and dichlorine monoxide in chemical equilibrium, wherein the rate of conversion of hypochlorous acid to dichlorine monoxide is held at a minimum by exclusion of rate increasing salts. Rate increasing salts such as, for example, those containing chloride ions can adversely impact the stability of antimicrobial solutions.

In another aspect, the antimicrobial solution can include one or more dichlorine monoxide generating catalysts. Exemplary catalysts can include any compound or species that functions as a buffer in the pH range (±about 1.5 pH units) of the product. For example, the catalyst can include: inorganic salts, such as phosphates; carboxylic acids, such as citric acid and acetic acid; nitrogen containing compounds, such as triethanolamine ("TEA"); and/or amines. Combinations of two or more catalysts may be used.

Preferred carboxylic acids have a pH within one pH unit of its pKa. Preferably, the catalyst is triethanolamine, sodium hypochlorite (NaOCl), chloride ion, phosphates, and/or citric acid.

The catalyst can be present in a variety of concentrations. In one aspect, the catalyst is typically present at a specific catalyst dependent concentration generally ranging from about 1 ppb to about 100 ppm and preferably from about 1 ppm to 10 ppm. When triethanolamine is used as the catalyst is present at a concentration ranging from 1 ppb to about 10 ppm, more preferably ranging from about 100 ppb to about 5 ppm, and even more preferably ranging from about 0.3 ppm to about 1.5 ppm.

When the catalyst is triethanolamine, the triethanolamine is preferably present in a concentration ranging from about 1 ppb to about 10 ppm, which correlates to a molarity of 1 to $10^{-8}$ M to 1 to $10^{-5}$ M, or more preferably from about 0.3 ppm to about 1.5 ppm. Further, triethanolamine is preferably employed as the catalyst at a pH of about 7, more preferably at a pH of about 5 to about 6.

When the catalyst is chloride ion. Preferably the catalytic chloride ion is present in a concentration ranging from about 30 ppm to about 5500 ppm, preferably from about 35 ppm to about 500 ppm, and more preferably from about 40 ppm to about 300 ppm, all preferably at a pH of 5.

The antimicrobial solution of the invention is compatible with a variety of pH levels. In fact, it has been found that changes in the pH can affect the equilibrium between hypochlorous acid and dichlorine monoxide preferably due to the catalytic effect of sodium hypochlorite. Suitable pH levels for the antimicrobial solution generally range from about 4 to about 10, preferably from about 5 to about 9, and more preferably from about 5 to 7.5, e.g., from about 5 to about 6.

In a further aspect, the antimicrobial solution can include a buffer. A wide variety of buffers can be employed, including, for example, phosphates, acetates, citrates, borates, and various other organic buffers.

In one aspect, the antimicrobial solution of the invention can be atomized for delivery to, e.g., sinus, oropharyngeal or pulmonary tissues. Suitable respiratory track conditions for treatment in accordance with the current invention are also disclosed in U.S. Patent Application Publication No. 2007/0196434.

A variety of techniques or methods can be employed to generate the antimicrobial solution of the invention. For example, the antimicrobial solution can be formed by first preparing a solution by dissolving $Cl_2$ gas in a dilute NaOH solution such that very low levels of chlorine are present and the pH is maintained in a range about 4-6 to minimize or exclude $Cl_2O$ in solution. The $Cl_2$ concentration can vary depending on the application. For example, suitable $Cl_2$ gas concentrations are generally from about 10 ppm to about 500 ppm (based on free available chlorine) and preferably from about 150 ppm to about 450 ppm (based on free available chlorine). The concentration of NaOH would be sufficient to yield the desired pH which is typically from about 4 to about 6, and preferably from about 4.5 to about 5.5, e.g., from about 5 to about 6.

The activated solution is made by buffering to a pH preferably ranging from about 5 to about 6, and adding a dichlorine monoxide generating catalyst to the solution. Buffering this solution at pH preferably in the range of about 5-6 generates a product of nearly pure HOCl. Through the addition of catalyst, it is possible to generate products ranging from HOCl to mixed HOCl/$Cl_2O$. This allows for efficient generation of $Cl_2O$ in accordance with the invention for various applications. In another preferred aspect, the catalyst is preferably selected from the group consisting of triethanolamine, sodium hypochlorite, and citric acid. Combinations of catalysts may also be used.

The antimicrobial solution can also be made by generating an oxidative-reductive potential water solution by electrolysis, buffering the solution to a pH preferably ranging from about 5 to about 6, and adding a dichlorine monoxide generating catalyst to the solution. The production of ORP water solutions are described in, for example, U.S. Patent Application Publication Nos. 2007/0196357 and 2005/0142157 A1 and U.S. Pat. No. 7,090,753, incorporated herein by reference. In another preferred aspect, the catalyst is selected from the group consisting of triethanolamine, sodium hypochlorite, and citric acid. Combinations of such catalysts may also be used.

In another aspect of the invention, an exemplary solution can be produced by dissolving $Cl_2$ gas in a dilute NaOH solution, buffering the solution to a pH preferably ranging from about 5 to about 6 with a suitable buffer, and adding triethanolamine until the concentration of this compound is preferably from about 0.3 ppm to about 1.5 ppm. It is thought that the activated solution of the invention may also have anti-inflammatory, anti-histamine, and/or vasodilating activity.

The antimicrobial solution of the invention can be employed for treating nasal or sinus infection by administering to the infected area an atomized antimicrobial solution including hypochlorous acid, dichlorine monoxide, triethanolamine, and a phosphate buffer. Preferably, triethanolamine is present in a concentration of about 0.3 ppm to about 1.5 ppm, and the pH of the solution is from about 5 to about 6.

The treatment of nasal or sinus infections can, e.g., also be achieved by: soaking an absorbent material with an antimicrobial solution that includes hypochlorous acid, dichlorine monoxide, triethanolamine, and a phosphate buffer. Preferably, triethanolamine is present in a concentration of about 0.3 ppm to about 1.5 ppm, and the pH of the solution is from about 5 to about 6; and inhaling the fumes of the soaked material via the nasal airways.

The antimicrobial solution can be administered in accordance with the invention parenterally, endoscopically, through a dialysis catheter or directly to the surface of any affected biological tissue, which may include the skin and/or one or more mucosal surfaces. Parenteral administration can include, for example, administering the antimicrobial solution intraperitoneally, intramuscularly, subcutaneously, intravenously, intra-arterially, intrathecally, intravesically or into a synovial space. Endoscopic administration of the antimicrobial solution can include using, e.g., bronchoscopy, colonoscopy, sigmoidoscopy, hysterscopy, laproscopy, athroscopy, gastroscopy or a transurethral approach. Administering the antimicrobial solution to a mucosal surface can include, e.g., administration to an esophageal, gastric, intestinal, peritoneal, urethral, vesicular, vaginal, uterine, fallopian, synovial mucosal surface, and nasal, and also can include administering the solution to an oral, tracheal, or bronchial mucosal surface. The antimicrobial solution provided by the invention can be administered to treat infections which have formed biofilms.

In accordance with the invention, the antimicrobial solution used can be administered topically, e.g., as a spray, mist, aerosol or steam, by any suitable method, e.g., by aerosolization, nebulization or atomization, e.g., in the form of droplets having a diameter in the range of from about 0.1 micron to about 100 microns, preferably from about 1 micron to about 10 microns. Methods and devices, which are useful for aerosolization, nebulization and atomization, are well known in the art. Medical nebulizers, for example, have been used to deliver a metered dose of a physiologically active liquid into an inspiration gas stream, e.g., for inhalation by a recipient. See, e.g., U.S. Pat. No. 6,598,602 (hereby incorporated by reference). Medical nebulizers can operate to generate liquid droplets, which form an aerosol, e.g., with an inspiration gas. In other circumstances medical nebulizers have been used to inject water droplets into an inspiration gas stream to provide gas with a suitable moisture content to a recipient, which is particularly useful where the inspiration gas stream is provided by a mechanical breathing aid such as a respirator, ventilator or anesthetic delivery system.

U.S. Pat. No. 5,312,281 (hereby incorporated by reference) describes an ultrasonic wave nebulizer, which atomizes water or liquid at low temperature and reportedly can adjust the size of mist. In addition, U.S. Pat. No. 5,287,847 (hereby incorporated by reference) describes a pneumatic nebulizing apparatus with scalable flow rates and output volumes for delivering a medicinal aerosol to neonates, children and adults. Further, U.S. Pat. No. 5,063,922 (hereby incorporated by reference) describes an ultrasonic atomizer. The antimicrobial solution also may be dispensed in aerosol form as part of an inhaler system for treatment of infections in the lungs and/or air passages or for the healing of wounds in such parts of the body.

For larger scale applications, a suitable device may be used to disperse the antimicrobial solution into the air including, but not limited to, humidifiers, misters, foggers, vaporizers, atomizers, water sprays, and other spray devices. Such devices permit the dispensing of the antimicrobial solution on a continuous basis. An ejector which directly mixes air and water in a nozzle may be employed. The antimicrobial solution may be converted to steam, such as low pressure steam, and released into the air stream. Various types of humidifiers may be used such as ultrasonic humidifiers, stream humidifiers or vaporizers, and evaporative humidifiers. The particular device used to disperse the antimicrobial solution may be incorporated into a ventilation system to provide for widespread application of the antimicrobial solution throughout an entire house or healthcare facility (e.g., hospital, nursing home, etc.).

Suitable surfaces for disinfection in accordance with the invention include, e.g., plastic surfaces, metal surfaces, glass surfaces, organic surfaces or a combination thereof. In particular, implanted medical and veterinary devices can be disinfected buy methods and products in accordance with the invention an artificial heart value, orthopedic appliance, implanted pacemaker, implanted tube, implanted stent, implanted mesh or a combination thereof. Additionally, surfaces which are all or part of a medical instrument, such as, e.g., surgical instruments, bronchoscope, colonoscope, sigmoidoscope, hysteroscope, laproscope, athroscope, gastroscope or cystoscope can be disinfected by methods and products which are embodiments of the invention.

The solutions of the invention can function as a low-level disinfectant capable of a four log ($10^4$) reduction in the concentration of live microorganisms, and also can function as a high-level disinfectant capable of a six log ($10^6$) reduction in concentration of live microorganisms. Suitable microorganisms include bacteria, fungi, yeasts, and viruses.

Examples of suitable microorganisms include, without limitation, *Pseudomonas aeruginosa, Escherichia coli, Enterococcus hirae, Acinetobacter baumannii, Acinetobacter* species, *Bacteroides fragilis, Enterobacter aerogenes, Enterococcus faecalis*, Vancomycin resistant-*Enterococcus faecium* (VRE, MDR), *Haemophilus influenzae, Klebsiella oxytoca, Klebsiella pneumoniae, Micrococcus luteus, Proteus mirabilis, Serratia marcescens, Staphylococcus aureus, Staphylococcus epidermidis, Staphylococcus haemolyticus, Staphylococcus hominis, Staphylococcus saprophyticus, Streptococcus pneumoniae, Streptococcus pyogenes, Salmonella choleraesuis, Shigella dysenteriae*, and other susceptible bacteria, as well as yeasts, e.g., *Trichophyton mentagrophytes, Candida albicans* and *Candida tropicalis*. Viruses including, e.g., adenovirus, human immunodeficiency virus (HIV), rhinovirus, influenza (e.g., influenza A), hepatitis (e.g., hepatitis A), coronavirus (responsible for Severe Acute Respiratory Syndrome (SARS)), rotavirus, respiratory syncytial virus, herpes simplex virus, varicella zoster virus, rubella virus, and other susceptible viruses.

For instance, the antimicrobial solution is capable of at least about five log ($10^5$), an about a six log ($10^6$), preferably at least an about a six log ($10^{6.5}$), more preferably at least an about a seven log ($10^7$) reduction in the concentration of a sample of live microorganism selected from the group consisting of *Pseudomonas aeruginosa, Escherichia coli, Enterococcus hirae, Acinetobacter baumannii, Acinetobacter species, Bacteroides fragilis, Enterobacter aerogenes, Enterococcus faecalis*, Vancomycin Resistant-*Enterococcus faecium* (VRE, MDR), *Haemophilus influenzae, Klebsiella oxytoca, Klebsiella pneumoniae, Micrococcus luteus, Proteus mirabilis, Serratia marcescens, Staphylococcus aureus, Staphylococcus epidermidis, Staphylococcus haemolyticus, Staphylococcus hominis, Staphylococcus saprophyticus, Streptococcus pneumoniae, Streptococcus pyogenes, Candida albicans* and *Candida tropicalis*, within 30 seconds of exposure, when measured at least two months after preparation of the antimicrobial solution.

Biofilms are surface attached microbial communities that can be found at almost any solid-liquid interface in industrial, environmental and clinical settings. There is compelling evidence that the biofilm lifestyle is an efficient means for microorganisms to define and maintain a protected niche. Biofilm associated infections cause significant morbidity and mortality. For example, the opportunistic bacterial pathogen *Pseudomonas aeruginosa* is responsible for persistent infections associated with cystic fibrosis (CF) lung disease, burn wounds, otorrhea, and the cornea. Other specific infections diseases associated with biofilms include, e.g., native valve endocarditis, otitis media, chronic bacterial prostatitis, and periodontitis. One of the factors contributing to the recalcitrant nature of these infections is the ability of *P. aeruginosa* to form biofilms in these tissues.

Bacteria growing in biofilms can become up to 1000-fold more resistant to antibiotics and other biocides as compared to their non-biofilm associated (or "planktonic") counterparts. As a result of this increased resistance, biofilm infections cannot be effectively treated with conventional antibiotic therapy. There is not a single mechanism that can be ascribed to the tenacious biofilm phenotype, which is believed to arise from a multiplicity of factors, including poor antimicrobial penetration, oxygen and nutrient limitation, slow growth, and adaptive stress responses.

In one embodiment, the antimicrobial solution of the invention can reduce a sample of live microorganisms including, but not limited to, *Escherichia coli, Pseudomonas aeruginosa, Staphylococcus aureus* and *Candida albicans*, from an initial concentration of between about $1 \times 10^6$ and about $1 \times 10^8$ organisms/ml to a final concentration of about zero organisms/ml within about one minute of exposure when measured at least about two months after preparation of the antimicrobial solution. This corresponds to from an about a six log ($10^6$) to about an eight log ($10^8$) reduction in organism concentration. Preferably, the antimicrobial solution is capable of achieving a $10^6$-$10^8$ reduction of *Escherichia coli, Pseudomonas aeruginosa, Staphylococcus aureus* or *Candida albicans* organisms when measured at least about six months after preparation, and more preferably when measured at least about one year after preparation.

Alternatively, the antimicrobial solution administered in accordance with the present invention can produce an about a six log ($10^6$), preferably an about a 6.5 log ($10^{6.5}$), more preferably an about a seven log ($10^7$) reduction in the concentration of a spore suspension of *Bacillus athrophaeus* spores within about five minutes of exposure when measured at least about two months after preparation of the antimicrobial solution. Preferably, the antimicrobial solution administered in accordance with the invention can achieve about a $10^6$ reduction in the concentration of *Bacillus athrophaeus* spores when measured at least about six months after preparation, and more preferably when measured at least about one year after preparation.

The antimicrobial solution of the invention also can produce about a four log ($10^4$), preferably an about a five log ($10^5$), more preferably an about a six log ($10^6$) reduction in the concentration of a spore suspension of *Bacillus athrophaeus* spores within about thirty (30) seconds of exposure when measured at least about two months after preparation of the antimicrobial solution.

The antimicrobial solution of the invention further can produce an about a six log ($10^6$), preferably an about a 6.5 log ($10^{6.5}$), more preferably an about a seven log ($10^7$) reduction in the concentration of fungal spores, such as *Aspergillis niger* spores, within about five to about ten minutes of exposure when measured at least about two months after preparation of the antimicrobial solution.

Alternatively, the antimicrobial solution administered in accordance with the invention preferably can yield at least about a $10^6$ reduction in the concentration of a sample of live microorganisms selected from the group consisting of *Escherichia coli, Pseudomonas aeruginosa, Staphylococcus aureus, C. perfingens, Neisseria gonorrhea, Chlamydia trachomatis, streptococci, enteroococci* and *Candida albicans*, and combinations thereof.

The antimicrobial solution of the invention further can produce more than 3 log ($10^3$), preferably more than 4 log ($10^4$), more preferably more than 5 log ($10^5$) reduction in the concentration of viruses, such as Human Immunodeficiency Virus (HIV) and adenovirus.

The inventive antimicrobial solutions can be used in combination therapy with, e.g., antibiotics, anti-inflammatory drugs, and the like. Suitable antibiotics can include, without limitation, penicillin, cephalosporins or other β-lactams, macrolides (e.g., erythromycin, 6-O-methylerythromycin, and azithromycin), fluoroquinolones, sulfonamides, tetracyclines, aminoglycosides, clindamycin, quinolones, metronidazole, vancomycin, chloramphenicol, antibacterially effective derivatives thereof, and combinations thereof. Suitable anti-infective agents also can include antifungal agents such as, for example, amphotericin B, fluconazole, flucytosine, ketoconazole, miconazole, derivatives thereof, and combinations thereof. Suitable anti-inflammatory agents can include, e.g., one or more anti-inflammatory drugs, e.g., one or more anti-inflammatory steroids or one or more non-steroidal anti-inflammatory drugs (NSAIDs). Exemplary anti-inflammatory drugs can include, e.g., cyclophilins, FK binding proteins, anti-cytokine antibodies (e.g. anti-TNF), steroids, and NSAIDs.

The invention provides methods of treating a skin ulcer in a patient by administering the activated hypochlorous acid solution in any suitable manner. For example, the activated solution may be administered to the patient by washing or irrigating the skin ulcer with the solution. Alternatively, the activated hypochlorous acid solution can be administered to the patient by soaking the skin ulcer in the solution. The skin ulcer can be soaked in the activated hypochlorous acid solution for any suitable length of time, generally for at least about one minute, and preferably for at least about two minutes.

In another embodiment, the activated hypochlorous acid solution can be administered to the patient by dressing the skin ulcer with a wound dressing saturated with the solution. The saturated wound dressing may be left in contact with the wound for a sufficient period of time to treat the wound. Preferably, the saturated wound dressing is changed periodically such as, for example, once a day or multiple times per day to provide a fresh dressing to the wound.

The invention further provides for a method of treating a skin ulcer preferably comprising: (1) washing or irrigating the ulcer with the activated solution; (2) soaking the ulcer in the activated solution; (3) dressing the ulcer with a wound dressing saturated with the activated solution, and, (4) optionally repeating steps (1)-(3). Additionally, a gel based on the activated solution could also be applied to dressings or gauzes for covering wounds. Steps (1)-(3) of the method may be repeated as often as necessary to treat the skin ulcer.

The skin ulcers may optionally be debrided either before or after the application of the activated hypochlorous acid solution to the wound. Preferably, the skin ulcer is debrided before applying the activated solution. The skin ulcer can also be debrided prior to the application of a wound dressing saturated with the ORP water solution.

Skin ulcers can be cleaned once a day by irrigation, washing, and/or soaking for the first 3-4 days to properly control the associated infection. The ulcers can be washed with soap and tap water, debrided, and sprayed with an activated hypochlorous acid solution once a day, b.i.d., t.i.d., q.i.d. or more frequently as needed. After cleaning, the ulcer can be soaked or otherwise moistened with the activated hypochlorous acid solution for any suitable period of time, generally from about 60 to about 120 minutes, preferably from about 15 to about 60 minutes, more preferably from about 5 to about 15 minutes. The ulcer may optionally be subject to further rising. Following the moistening of the skin ulcer, the wound is preferably covered up with a moistening gel (the active principle of which can be an ORP water solution) and a dry dressing is applied. The moistening gel can further comprise an activated solution. Optionally, this procedure is repeated once a day, b.i.d., t.i.d., q.i.d. or more frequently, for the first 72 hours of the treatment. Thereafter, it can be optionally repeated once every 3 to 4 days, according to the clinical evaluation.

The patient treated according to the invention can be a human or veterinary patient (e.g., a non-human mammal). The skin ulcers to which the activated hypochlorous acid solution is applied can be located anywhere on a patient, including without limitation, wherein the skin ulcer is located on the head, neck, upper extremity, hands, fingers, trunk, genitalia, lower extremity, foot, toes, paws, hooves or combinations thereof. Multiple skin ulcers on one patient can be treated at the same time.

The invention provides for the treatment of skin ulcers of any depth, shape or size. Skin ulcers suitable for treatment include, by way of example, ulcers limited to the superficial epidermis, ulcers which preserve the epidermal basal layer, ulcers penetrating the epidermis, ulcers involving the dermis, ulcers which penetrate through the dermis into the subcutaneous tissue, and ulcers which penetrate to deep tissues including muscle, fat, and bone. The skin ulcers can be any shape, for example, round, oval, linear, or irregularly shaped. Skin ulcers having any suitable surface area can be treated including, for example, a surface area of at least about 1 mm2, at least about 5 $mm^2$, at least about 1 $cm^2$ or at least about 2 $cm^2$.

The invention provides for methods of treating a skin ulcer in a patient, wherein the skin ulcer is caused by, for example, arterial insufficiency, venous insufficiency, lymphatic insufficiency, neuropathy, pressure, trauma or a combination thereof.

Various types of skin ulcers in a patient can be treated with the activated hypochlorous acid solution according to the invention. For example, the following skin ulcers are suitable for treatment: diabetic foot ulcer, ischemic ulcer, gangrenous ulcer, venous stasis ulcer, decubitus ulcer or traumatic ulcer. In addition, the invention provides for methods of treating skin ulcers in patients with arterial insufficiency wherein the arterial insufficiency is caused by, for example without limitation, atherosclerosis, hypertension, smoking, emboli, diabetes, arterial inflammation, graph-versus-host disease, Raynaud's Disease, Buerger Disease (Thromboangiitis Obliterans) or combinations thereof.

The invention further provides methods of treating skin ulcers in patients with venous insufficiency caused by, for example without limitation, congestive heart failure, phlebitis, blood clots, venous valvular abnormalities, hereditary factors or combinations thereof. Skin ulcers may also be treated in patients with intravascular blood flow abnormalities caused by, for example without limitation, Sickle Cell Anemia, hypercoagulable states, leukostasis, hypervisousity syndromes, DIC or combinations thereof.

The invention also provides for methods of treating skin ulcers in patients with lymphatic insufficiency wherein the lymphatic insufficiency is caused by, for example without limitation, tumor emboli, filarasis or combinations thereof. Similarly, the invention provides for methods of treating skin ulcers in patients with edema wherein the edma is caused by, for example without limitation, congestive heart failure, hepatic cirrhosis, the nephrotic syndrome, malnutrition or combinations thereof.

The invention includes methods for the treatment of pressure skin ulcers wherein the pressure ischemia results from the patient's immobility, paralysis, obesity or combinations thereof. The invention additionally provides for methods of treatment of skin ulcers in patients with neuropathies wherein the neuropathies are caused by, for example without limitation, diabetes, uremia, toxins, amyloid, multiple sclerosis, hereditary neuropathy or combinations thereof.

The invention also provides for methods of treating a skin ulcer in a patient, wherein the skin ulcer is caused by a metabolic disorder (such as, e.g., diabetes, gout), inflammatory condition (such as, e.g., lupus, mixed connective tissue disease, rheumatoid arthritis, any type of primary or secondary vasculitis, hypersensitivity reactions, erythema multiforme, bullous skin diseases, pemphigus vulgaris), infectious disease (such as, e.g., herpes, leprosy, varicella-zoster, sepsis), neoplasm (such as, e.g., skin cancer, hemangiomas), degenerative disease (such as, e.g, scleroderma, morphea), hereditary disease (such as, e.g., Sickle Cell Anemia), trauma/environmental insults (such as, e.g., abrasions, radiation, post operative fistulas) or a combination thereof.

Skin ulcers can be treated with the activated hypochlorous acid solution, e.g., the activated ORP water solution in combination with other therapies in accordance with the invention. For example, without limitation, venous stasis leg ulcers can be treated by administering an activated hypochlorous acid solution as part of a comprehensive outpatient treatment which can include sclerotherapy in as many veins as needed. Following each sclerotherapy session, the patient can wear a Class 2 compression stocking to assist closure of the treated veins. The length of time the stocking needed to be worn varied from about three days to about three weeks depending on the size of the veins injected. Compressive bandage is optionally used. Saphenectomy, can also be performed in suitable patients.

The invention further provides for methods of treating a skin ulcer, wherein the skin ulcer is a foot ulcer in a diabetic patient. The invention provides for a method of treating a foot ulcer in a diabetic patient can include, e.g.: (1) debriding the ulcer; (2) washing or irrigating the ulcer with the activated water solution; (3) soaking the ulcer in the solution for at least two minutes; (4) drying the ulcer for at least about two minutes; (5) dressing the ulcer with a wound dressing saturated with the solution; and (6) optionally repeating steps (1)-(5), wherein the ulcer is an infected Grade 2 or Grade 3 foot ulcer in a diabetic patient, said ulcer having a surface area of at least about 2.0 cm2. Such a method for treating foot ulcer in a diabetic patient can comprise repeating steps (1)-(5) any suitable number of times until the ulcer is substantially healed. Preferably, steps (1)-(5) are repeated at least one time. Suitable ulcers for treatment in accordance with the current invention are also disclosed in U.S. Patent Application Publication No. 2006/0235350.

A therapeutically effective amount of the activated hypochlorous acid solution, can be delivered to the peritoneal space, e.g., by gravity (e.g., by pouring or dispensing the activated hypochlorous acid solution from a container or device) or by delivering the activated hypochlorous acid solution under pressure (e.g., by spraying). One or more flushings of the peritonium can be performed, i.e., the peritonium can be "lavaged." The activated hypochlorous acid solution can be retained in the peritoneal cavity for any suitable length of time, e.g., a period of time effective to provide a therapeutic response, e.g., seconds, minutes, hours, or days, and optionally removed using any suitable method. Suitable methods of removal can include, e.g., allowing the activated hypochlorous acid solution to be naturally absorbed into one or more surrounding tissues, blotting with one or more absorbent materials (e.g., gauze, sponge, towel, or mesh), removal by suction, and the like, and combinations thereof.

In one embodiment, the method of the present invention includes: accessing the peritoneal space in a patient, e.g., that has or is at risk of developing peritonitis or that is at risk of developing adhesions or abscesses associated with peritonitis; delivering to the patient's peritoneal space a volume of the activated hypochlorous acid solution that is sufficient to contact peritoneal tissue with a therapeutically effective amount thereof; allowing the activated hypochlorous acid solution to remain in the peritoneal space for a period of time sufficient to provide a therapeutic effect; optionally, removing the activated hypochlorous acid solution from the peritoneal space; and, optionally, repeating the peritoneal lavage.

The peritoneal space can be accessed by any suitable method, e.g., surgically or transabdominally, through the opening of an existing wound, and the like. Any suitable volume of the activated hypochlorous acid solution can be delivered to the peritoneal space, e.g., from about 0.01 to about 10 liters (e.g., from about 0.1 to about 10 liters, from about 0.2 to about 10 liters, from about 0.5 to about 10 liters, or from about 1 to about 10 liters). The activated hypochlorous acid solution can optionally be removed and, if desired, the lavages repeated, e.g., as described herein. The lavage(s) can be performed alone or in combination with additional therapies, e.g., in combination with one or more sterile saline lavages, antibiotic therapy, and combinations thereof.

The activated hypochlorous acid solution can be administered endoscopically, through a dialysis catheter or directly to the surface of any affected biological tissue, which may include the skin and/or one or more mucosal surfaces. Parenteral administration can include, for example, administering the activated hypochlorous acid solution intraperitoneally, intramuscularly, subcutaneously, intravenously, intraarterially, intrathecally, intravesically or into a synovial space. Endoscopic administration of the activated hypochlorous acid solution can include using, e.g., bronchoscopy, colonoscopy, sigmoidoscopy, hysterscopy, laproscopy, athroscopy, gastroscopy or a transurethral approach. Administering the activated hypochlorous acid solution to a mucosal surface can include, e.g., administration to an esophageal, gastric, intestinal, peritoneal, urethral, vesicular, vaginal, uterine, fallopian, synovial mucosal surface, and nasal, and also can include administering the solution to an oral, tracheal, or bronchial mucosal surface.

The present invention additionally provides a method of treating impaired or damaged tissue, such as wounds from any cause, which method comprises contacting the impaired or damaged tissue with a therapeutically effective amount of an activated hypochlorous acid solution, e.g., an activated ORP water solution. The method includes treating tissue, which has been impaired or damaged by surgery or which has been impaired or damaged by causes that are not necessarily relate to surgery, e.g., burns, cuts, abrasions, scrapes, rashes, ulcers, puncture wounds, infections, and the like.

The method of the present invention can be used in the treatment of tissues, which have been impaired or damaged, e.g., by surgery. For instance, the method of the present invention can be used for treating tissues, which have been impaired or damaged by an incision. In addition, the method of the present invention can be used for treating tissues, which have been impaired or damaged by oral surgery, graft surgery, implant surgery, transplant surgery, cauterization, amputation, radiation, chemotherapy, and combinations thereof. The oral surgery can include, for example, dental surgery such as, e.g., root canal surgery, tooth extraction, gum surgery, and the like. Suitable tissue injuries for treatment in accordance with the current invention are also disclosed in U.S. Patent Application Publication No. 2007/0173755.

The method of the present invention also includes treating tissues, which have been impaired or damaged by one or more burns, cuts, abrasions, scrapes, rashes, ulcers, puncture wounds, combinations thereof, and the like, which are not necessarily caused by surgery. The method of the present invention also can be used for treating impaired or damaged tissue, which is infected, or tissue impaired or damaged due to infection. Such infection can be caused by one or more infectious pathogens, such as, e.g., one or more microorganisms selected from the group consisting of viruses, bacteria, and fungi, as described herein.

In a preferred embodiment, the activated hypochlorous acid solution of the invention may be administered to treat patients with first, second or third degree burns. Patients having a combination of burns, such as second and third degree burns, may also be treated with the ORP water solution. First degree burns affect the epidermis, or skin surface. Second degree burns affect the epidermis and the underlying dermis. Third degree burns affect the epidermis, dermis and the hypodermis. More preferably, the activated hypochlorous acid solution is administered to treat patients with second or third degree burns. Burns that are suitable for treating according to the invention are caused by various injuries, including, for example, contact with fire, boiling liquids (e.g., water, milk, etc.), or electricity, and generally extend to from about 0% to about 69% of the patient's tissue.

The activated hypochlorous acid solution may be administered to patients with burns in any suitable manner. The activated hypochlorous acid solution may be administered topically by spraying, bathing, soaking, wiping or otherwise moistening the burn. The activated hypochlorous acid solution is administered in an amount sufficient to treat the burn. The activated hypochlorous acid solution is administered to a burn at least once a day and preferably more than once per day. More preferably, the activated hypochlorous acid solution is administered to a burn three times per day.

The activated hypochlorous acid solution may be applied directly to the burn area, for example, by pouring from a container or spraying from a reservoir. The burn may be sprayed using any suitable device. Preferably, a high-pressure irrigation device is used to spray the activated hypochlorous acid solution over the burn.

The burn may be soaked by submersing the burn either partially or completely in the ORP water solution. The burn may soak for any suitable period of time. Generally, the burn is soaked in the activated hypochlorous acid solution for at least about one minute. Preferably, the burn is soaked for about 5 minutes to about 15 minutes.

Alternatively, the activated hypochlorous acid solution may be applied to the burn using a substrate such as, for example, gauze, that has been saturated with activated ORP water. Preferably, the activated hypochlorous acid solution is applied by multiple methods including spraying and the burn is both sprayed and soaking.

The burn may optionally be dressed by applying a moist wound dressing saturated with the activated hypochlorous acid solution, e.g., an activated ORP water solution. In addition to the moist wound dressing, the burn may optionally be dressed with dry gauze and an adhesive covering. Any suitable suave, cream, gel and/or ointment may also be applied to the burn surface after the administration of the activated hypochlorous acid solution, e.g., an activated ORP water solution.

In one embodiment, a patient having a burn requiring treatment is subject to a washing procedure using the activated hypochlorous acid solution of the invention. The activated hypochlorous acid solution is first sprayed on the burn using a high-pressure irrigation device. Next, the burn is soaked in the activated hypochlorous acid solution for a suitable period of time. After soaking, the burn is then sprayed with the activated hypochlorous acid solution again. The burn is then allowed to sit in a moistened state for at least five minutes. This procedure is carried out at least once a day on a patient's burn, preferably twice a day, and more preferably three times per day.

Prior to the administration of the activated hypochlorous acid solution, e.g., an activated ORP water solution, the burn is preferably subject to debridement therapy to remove hyperkeratinized, necrotic, and otherwise unhealthy tissue down to healthy appearing tissue. In debriding the burn, the wound margins are excised to healthy bleeding tissue. The burn may be cleaned of debris after debridement.

If necessary, administration of activated hypochlorous acid solution can be used in combination with skin grafts to promote healing of the burn. The administration of activated solution optionally be combined with the administration of topical and/or systemic antibiotics. Suitable antibiotics include cephalosporins (e.g., cefotaxime, ceftriaxone, etc.), carbapenems, monobactams, penicillins and the like. Preferably, the activated hypochlorous acid solution is applied to the burn without the administration of an antibiotic.

In another embodiment of the invention, a second and/or third degree burn on a patient is initially debrided and then preferably sprayed with the activated hypochlorous acid solution with a high-pressure irrigation device. The amount of activated hypochlorous acid solution used to wash the burn is preferably sufficient to remove debris. The burn is then preferably soaked in the activated hypochlorous acid solution for a suitable period of time. The patient's burn is next sprayed with ORP water solution, and the solution is allowed to moisten the burn for a suitable period of time, preferably about 5 minutes to about 15 minutes. The spraying and moistening is repeated three times a day. In between the administrations of ORP water solution, the surface of the burn is preferably not dressed.

The process of high-pressure spraying, optionally soaking, spraying, and moistening the burn may be repeated at suitable intervals. Preferably, the procedure in which the burn is high-pressure sprayed, optionally soaked, sprayed, and moistened is repeated once per week and more preferably, once per day. The treatment of the burn using the activated hypochlorous acid solution may continue until the burn is sufficiently healed which typically requires repeating the procedure over several days. Generally, the activated hypochlorous acid solution is applied every day for at least three days. Typically, the activated hypochlorous acid solution is applied every day for at least five days, preferably for at least seven days, and more preferably for at least ten days. The healing of the burn is typically measured by the rate of scar contraction and epithielization. Suitable burns for treatment in accordance with the current invention are also disclosed in U.S. Patent/No. 20060241546.

The present invention also relates to a method of using an activated hypochlorous acid solution as an irrigant in an oral or maxillo-facial dental procedure by administering an activated hypochlorous acid solution to a patient in an amount sufficient to irrigate the site. In a preferred embodiment, the activated hypochlorous acid solution of the invention can be utilized in a variety of dental applications. First, the activated hypochlorous acid solution can be administered to patients for the routine disinfection of the oral cavity as part of an on-going program of oral hygiene. Second, the activated hypochlorous acid solution can be used to irrigate and/or disinfect oral tissues, tooth surfaces, cavities, or a tooth canal during oral or maxillo-facial procedures. Third, the activated hypochlorous acid solution can be administered to treat patients with damage to the oral tissues caused by, for example, oral or maxillo-facial procedures or disease. Finally, the activated hypochlorous acid solution can be used to disinfect objects related to dentistry, including, for example, dental instruments, irrigation lines of a dental office irrigation system, and dentures.

In one embodiment, the activated hypochlorous acid solution can be administered to patients for the routine disinfection of the oral cavity as part of an on-going program of oral hygiene. The activated hypochlorous acid solution can reduce levels of a wide spectrum of oral micro-organisms present in the oral cavity, thereby decreasing the occurrence of infectious diseases. The activated hypochlorous acid solution is administered to patients in any suitable manner. Preferably, the activated hypochlorous acid solution is administered as a mouthrinse or mouthwash. Preferably, patients rinse for at least about 30 seconds, more preferably for at least about one minute, and most preferably for at least about two minutes. Patients rinse daily, for example, or twice a day, or three times a day. Preferably, patients should rinse with activated hypochlorous acid solution after meals. Patients should brush and floss their teeth daily in combination with rinsing with ORP water solution. Patients can, for example, brush and floss their teeth before rinsing with the ORP water solution.

The reduction in oral microbial flora upon rinsing with the activated hypochlorous acid solution can be monitored. Oral microbial flora levels are measured by culturing bacteriological swabs taken from the buccal mucosa. First, a baseline bacteriological swab is taken. The immediate reduction in oral microbial flora upon rinsing with activated hypochlorous acid solution can be determined by taking bacteriological swabs about ten minutes after rinsing and about fifteen minutes after rinsing. The long term reduction in oral microbial flora after a regimen of rinsing can also determined. For example, bacteriological swabs can be taken after one month of rinsing with the activated solution.

In a second embodiment, the activated hypochlorous acid solution can also be used as an irrigant and/or disinfectant during oral or maxillo-facial procedures. The activated hypochlorous acid solution can be used as the irrigant in ultrasonic scaling. Ultrasonic scaling is a procedure for the treatment of periodontal disease that removes plaque above and below the gum line. The ultrasonic scaler is operated in conjunction with a coolant or irrigant, and the cavitational activity within the solution contributes to the disruption and removal of plaque. Typically, the irrigant is water. The use of activated hypochlorous acid solution instead of water can slow the recolonization of microbes after removal of plaque. The treatment can be monitored with an assessment of inflammation, bleeding and pocket depths. The ultrasonic scaling with activated hypochlorous acid solution as the irrigant can be combined with other follow up treatments. The patient should brush and floss teeth daily. Preferably, the ultrasonic scaling is combined with the outpatient administration of activated hypochlorous acid solution in the form of a rinse. The patient rinses with activated hypochlorous acid solution for at least about two months or preferably at least about three months after the ultrasonic scaling procedure.

The activated hypochlorous acid solution is used an irrigant to cleanse and disinfect a cavity or a tooth canal during tooth restoration. Treatment for tooth decay or cavities consists of removing the decayed material and replacing it with restorative, or filling, material. First, the decayed material is removed by drilling. Next, the tooth is prepared for filling, including the steps of cleaning and disinfecting the dentin surface and/or enamel. The activated hypochlorous acid solution can be used as an irrigating solution to wash away debris such as debrided tooth material. Alternatively, the activated hypochlorous acid solution can be used to disinfect the dentin surface and/or enamel prior to filling. The activated hypochlorous acid solution can be applied by spraying the surface or moistening the surface with a brush or sponge. Similarly, the activated hypochlorous acid solution can be used as an irrigating solution during endodontic, or root canal, therapy. Endodontic therapy is required if the patient has a bacterial infection in a tooth's nerve tissue. Endodontic therapy consists of making an access hole to the pulp chamber with a drill, cleaning out the interior of the tooth, filling and sealing the interior of the tooth with root canal filling material, and filling in the access hole. As part of the cleaning step, irrigants are used to dissolve and flush out debris. The activated hypochlorous acid solution can be used as the irrigant during endodontic therapy. Alternatively, the activated hypochlorous acid solution can be used to disinfect the interior tooth after cleaning and prior to filling.

The activated hypochlorous acid solution is used as an irrigant and/or antiseptic during tooth extraction. After the tooth is extracted, the socket is irrigated with the activated hypochlorous acid solution to dissolve and flush out debris. The socket can be irrigated for at least about 30 seconds, or at least about one minute, or at least about two minutes, or longer if required. Preferably, the activated hypochlorous acid solution is used when the tooth is extracted due to an abscess or periodontal disease.

The activated hypochlorous acid solution can be used as an irrigant and/or intraoperative antiseptic during maxillo-facial surgeries. Two recurrent problems in maxillo-facial surgery are bleeding and infection. The activated hypochlorous acid solution reduces bleeding in the surgical field. The activated hypochlorous acid solution also can decrease post-operative healing time.

The activated hypochlorous acid solution is administered to patients undergoing maxillo-facial surgeries in any suitable manner. The activated hypochlorous acid solution can be administered immediately before, during, or immediately after the surgery. For example, the entire oral cavity can be rinsed once, twice, or three times prior to an incision. Preferably, the oral cavity is rinsed twice. The activated hypochlorous acid solution can be used to irrigate the operation site. Preferably, the activated hypochlorous acid solution is used to the flush operation site prior to suturing. The operation site can be irrigated for at least one minute, or at least two minutes, or at least three minutes, or longer if required.

In yet another embodiment, the activated hypochlorous acid solution may be administered to patients with oral tissues damaged by disease or an oral or maxillo-facial procedure. Preferably, the activated hypochlorous acid solution is administered to patients suffering from periodontal diseases. Periodontal disease is a chronic bacterial infection that affects the gums and bone supporting the teeth and is one of the leading causes of tooth loss. Disease causing bacteria are present in the plaque above and below the gum line. Examples of periodontal diseases include gingivitis, or inflammation of the gingival tissues, and periodontitis, an inflammatory disease of the periodontium. Treatment with activated hypochlorous acid solution results in arresting the infection. There is also a reduction or elimination of inflammation and bleeding. Furthermore, in many cases, treatment with activated hypochlorous acid solution results in bone regeneration, halting the loss of periodontal attachment.

The activated hypochlorous acid solution can be administered to patients suffering from periodontal diseases in any suitable manner. Preferably, the activated hypochlorous acid solution is administered as a mouthrinse or mouthwash. Preferably, patients rinse for at least about 30 seconds, more preferably for at least about one minute, and most preferably for at least about two minutes. Patients rinse daily, or twice a day, or preferably three times a day. Preferably, patients should rinse with activated hypochlorous acid solution after meals. Patients should brush and floss their teeth daily in combination with rinsing with activated solution. The treatment of periodontal disease using the activated hypochlorous acid solution may continue until the disease is resolved. Depending on the progression of the disease, the activated hypochlorous acid solution can be administered for at least about one month, or preferably about two months, or more preferably about three months, or longer. The administration of the activated hypochlorous acid solution can be combined with other treatments for periodontal diseases. Such treatments include mechanical removal of plaque and calculus and administration of antibiotics. Preferably, administration of the activated hypochlorous acid solution is combined with mechanical removal of plaque and calulus. Preferably, administration of the activated hypochlorous acid solution is not combined with antibiotics.

The activated hypochlorous acid solution can also be administered to patients with oral mucosal lesions or ulcers. Lesions are accompanied by pain and redness, and can impair chewing and swallowing. The lesions or ulcers have many causes. For example, denture stomatitis are lesions caused by wearing dentures. Patients who are immuno-compromised are also more likely to develop oral mucosal lesions or ulcers. Oral candidiasis, a fungal infection of the mucous membrane, causes lesions around the mouth. Oral mucositis is a common side effect experienced by patients undergoing cancer treatment, such as chemotherapy, radiation, or bone marrow transplant.

The activated hypochlorous acid solution can be administered to patients suffering from oral mucosal lesions or ulcers in any suitable manner. Preferably, the activated hypochlorous acid solution is administered as a mouthrinse or mouthwash. Preferably, patients rinse for at least about 30 seconds, more preferably for at least about one minute, and most preferably for at least about two minutes. Patients rinse daily, or twice a day, or more preferably three times a day. The treatment of oral mucosal lesions or ulcers using the activated hypochlorous acid solution may continue until the lesions or ulcers are healed. Depending on the progression of the disease, the activated hypochlorous acid solution can be administered for about two weeks, for example, or about three weeks, or about four weeks, or about two months, or longer. The administration of the activated hypochlorous acid solution may be prophylactic in patients who are susceptible to oral mucosal lesions or ulcers.

The activated hypochlorous acid solution can be administered to patients after undergoing an oral or maxillo-facial procedure in any suitable manner. Preferably, the activated hypochlorous acid solution is administered as a mouth-rinse or mouthwash. Preferably, patients rinse for at least about 30 seconds, more preferably for at least about one minute, and most preferably for at least about two minutes. Patients rinse daily, or preferably twice a day, or more preferably three times a day. The activated hypochlorous acid solution can be administered for about one week, or for about two weeks, or for about one month, or for about three months, or longer if necessary. The activated hypochlorous acid solution can be administered in combination with NSAID. The activated hypochlorous acid solution can also be administered in combination with antibiotics. Preferably, no antibiotic is administered. Suitable dental and oral lesions for treatment in accordance with the current invention are also disclosed in U.S. Patent Application Publication No. 2006/0253060.

The activated hypochlorous acid solution may be applied to disinfect and sterilize dental equipment. For example, to disinfect and sterilize dental instruments, the instrument can be maintained in contact with the activated hypochlorous acid solution for a sufficient period of time to reduce the level of organisms present on the equipment to a desired level. To disinfect and sterilize dental office irrigation lines, for example, the irrigation lines are flushed with the activated solution. The reduction in bacteria levels can be measured by taking bacterial cultures before and after flushing the lines.

The activated hypochlorous acid solution administered in accordance with the present invention also can be used as the irrigation solution for hydrosurgery devices that are used to debride oral lesions. Suitable hydrosurgery devices can include, for example, the VersaJet devices sold in the United States by Smith and Nephew, Debritom in Europe by Medaxis, JetOx in the United States and Europe by DeRoyal or PulsaVac in Italy. It is believed that the activated hypochlorous acid solution can act synergistically with the device by reducing the microbial load in the oral lesions and by avoiding the formation of infectious mists during the debridement procedure. Thus the device may be used to debride an oral lesion with continuous irrigation, reduce the infection process and avoid the formation of infectious mists in accordance with the present invention.

The following examples further illustrate the invention but, of course, should not be construed as in any way limiting its scope.

EXAMPLE 1

This example demonstrates a method of determining the rate of dichlorine monoxide formation.

In dilute solution, hypochlorous acid is in equilibrium with minute amounts of dichlorine monoxide:

$$2HOCl \leftrightharpoons Cl_2O + H_2O$$

The large excess of water pushes the equilibrium towards HOCl so in solution there is hardly any dichlorine monoxide present. What is important, however, is the rate at which HOCl is converted to $Cl_2O$. This reaction is catalyzed by a number of different chemicals. Since $Cl_2O$ is significantly more reactive with certain chemicals than HOCl, it is possible to determine the rate of formation of $Cl_2O$ through the reaction rate of the solution with an indicator chemical. Four-hydroxy benzoic acid ("4OH BA") is used as this indicator compound in what is believed to be the following reaction:

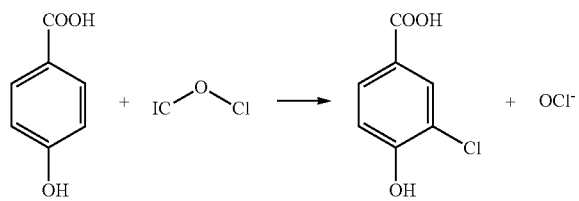

The reaction rate of 4OH BA is determined by measuring the UV absorption at 250 nm over time of a mixture of 4OH BA with a test solution. This wavelength was chosen to maximize 4OH BA absorption and minimize HOCl absorbance. In the procedure, a solution containing an excess of 4OH BA is mixed with the test solution in a quartz cuvette. The UV absorption of the solution at 250 nm is measured over a 2 minute period. The rate (slope of the line) at time=0 is equivalent to the reaction rate. Typical curves for a reaction at pH 6, pH 7, and with a catalyst added are shown in FIG. 1.

In FIG. 1, the initial UV absorbance is equivalent to the UV absorbance of the indicator plus HOCl. The second point on the curve is the first measured value once the cuvette is placed in the UV spectrometer (12 seconds). While not an exact measurement of the loss of 4OH BA, this is an indirect way of looking at the relative rate of reaction and, therefore, the amount of $Cl_2O$ present.

EXAMPLE 2

This example demonstrates the production of dichlorine monoxide in accordance with the invention.

Figure 2:
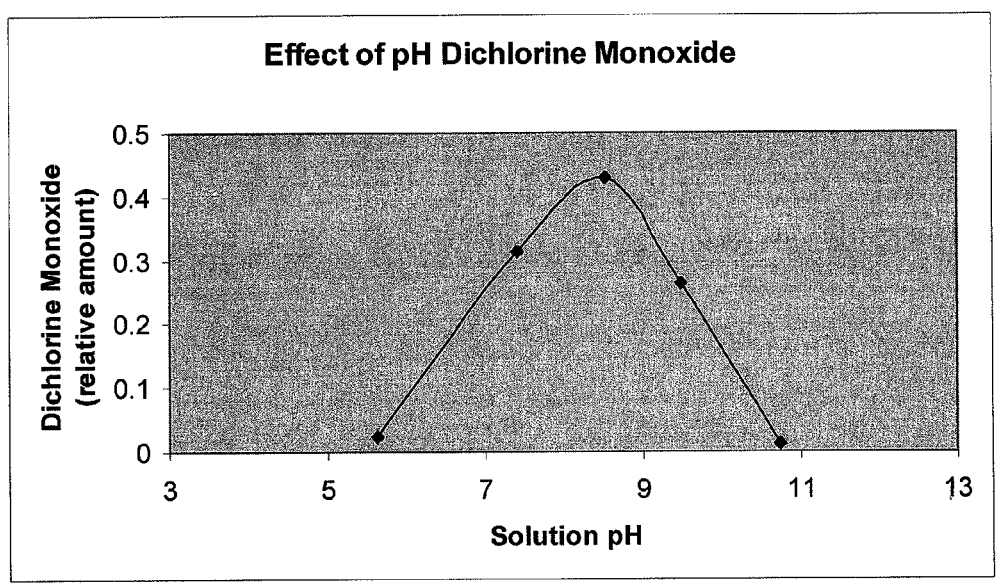
FIG. 2. The catalytic effect of hypochlorite on the formation of dichlorine monoxide (very low chloride solution).
Figure 3:
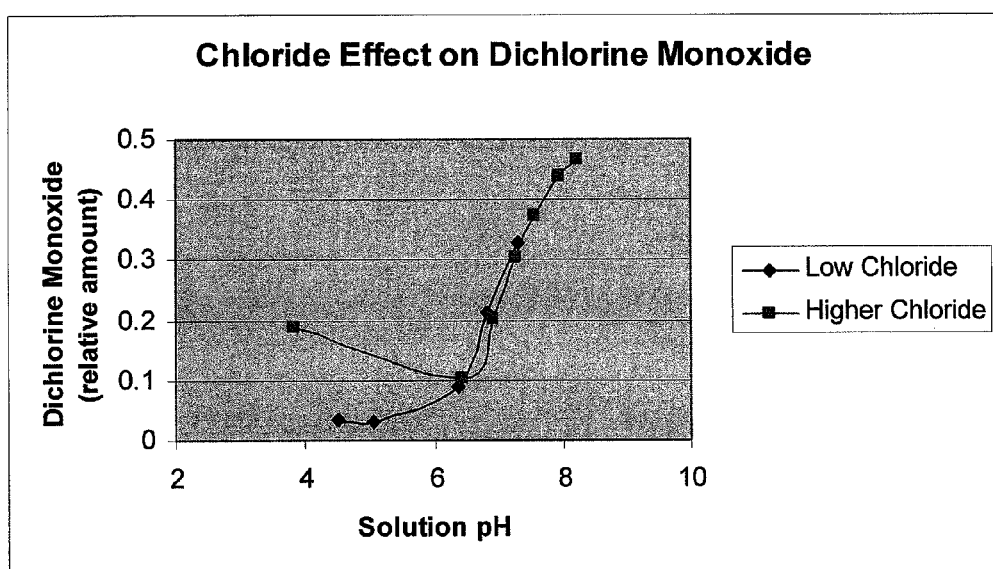
FIG. 3. Effect of chloride ion on the formulation of dichlorine monoxide.
Figure 4:
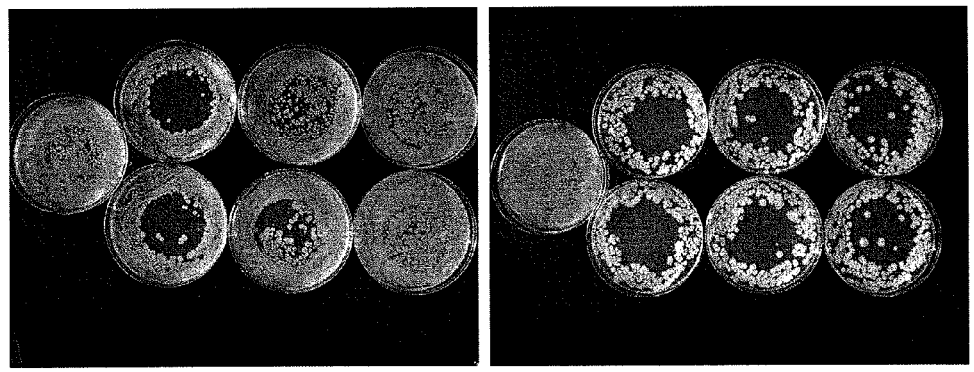
FIG. 4. Picture on left at 0.3 ppm TEA (chemically produced). Picture on right 1.5 ppm TEA (electrolysis produced). Petri dish on left of each picture is control. Plates from right to left in each picture are 1 minute, 5 minute, 30 minute exposure time.

The pH dependence of the $Cl_2O$ concentration in a hypochlorous/hypochlorite solution is shown in FIG. 2. The catalytic effect of chloride ion on the formation of dichlorine monoxide is most effective at a higher pH range (pH>5). This can be seen in FIG. 3 for two exemplary pre-antimicrobial hypochlorous/hypochlorite containing solutions. The solution with low chloride ion concentration shows very little $Cl_2O$ formation between pH 4-6. At higher chloride content, the chlorinating ability of the solution at pH 4 is much greater. The chlorinating ability at this pH is due to a combination of the formation of dichlorine monoxide and also chlorine gas. Increasing chloride ion will shift this point to a higher pH. Once the pH reaches 6, the effect due to hypochlorite ion overshadows the chloride effect.

These results indicate that the amount dichlorine monoxide present in a hypochlorous/hypochlorite solution is chloride ion and pH dependent.

EXAMPLE 3

This Example demonstrates spore killing activity of an exemplary activated hypochlorous acid solution in the wound.

This Example studied the minimum amount of Free Available Chlorine (FAC) needed in an activated hypochlorous acid solution at pH levels between 5.5 and 8.5 to demonstrate efficacy in the spore kill test. Additionally, the effect of hypochlorous acid (HOCl) content on product efficacy in this pH range was examined. The data obtained show that as solution pH increases, higher concentrations of FAC are needed in order to show the same efficacy against spores.

Figure 5:
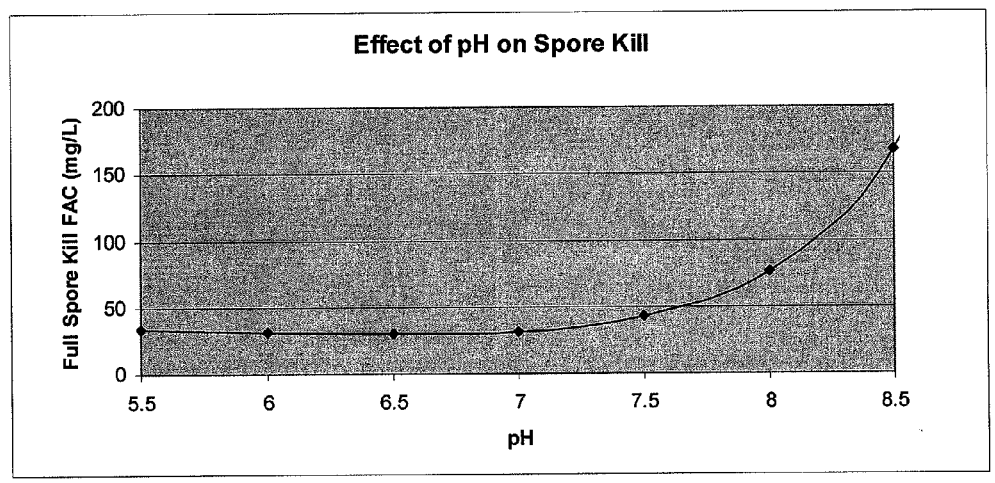
FIG. 5 pH dependent spore killing with an exemplary activated hypochlorous acid solution, e.g., an activated ORP water solution.

The spore kill test is a suspension test in which spores are suspended in product, and then exposed for ten minutes. The solution is then neutralized and plated. The plates are incubated and checked for bacterial growth. FAC levels showing "complete kill" are those solutions whose plates show no growth. The results are presented in FIG. 5 and indicate the desirability of maintaining a pH of less than about 7.5 in the treated tissue.

An exemplary activated hypochlorous acid solution was diluted and pH adjusted to make solutions with a pH ranging from 5.5-8.5 and FAC concentrations between 20 and 77 ppm. These solutions were then tested in the spore kill efficacy test. The results of this analysis are presented in the following table:

TABLE 1

| Sample pH | Minimum FAC concentration showing near complete kill (ppm) |
|---|---|
| 5.5 | 32.9 |
| 6.0 | 29.2 |
| 6.5 | 32.9 |
| 7.0 | 32.9 |
| 7.5 | 36.9 |
| 8.0 | 77.1 |
| 8.5 | 166.0 |

Solutions of product at FAC 20 ppm were made to be either 0.2M NaClO$_4$ or 200 ppm chloride at pH 6 and pH 7 and were tested for efficacy against spores. The chloride and NaClO$_4$ solutions showed near complete kill after 15 minutes at both pH levels. The results of this analysis are presented in the following table:

TABLE 2

| pH | Salt | Avg. plate count | | |
|---|---|---|---|---|
| | | 10 min | 15 min | 20 min |
| pH 6 | NaCl | 10 | 0 | 0 |
| | NaClO$_4$ | 1 | 8 | 1 |
| pH 7 | NaCl | 177 | 0 | 0 |
| | NaClO$_4$ | 37 | 0 | 1 |

EXAMPLE 4

This Example demonstrates antimicrobial activity of an exemplary activated hypochlorous acid solution in the wound in the presence of a high organic load of albumin.

E. coli, S. aureus, and P. aeruginosa were tested against three different FAC solutions in the presence of organic load in the form of albumin. After 30 second exposures, 500 μL aliquots were plated onto sterile agarose plates and incubated to allow for growth. Plates were checked at 24 and 48 hours. Cell colonies were counted and recorded.

Activated hypochlorous acid solution, e.g., an activated ORP water solutions used were:
1. 71.9 ppm FAC, pH 7.0
2. 72.8 ppm FAC, pH 4.9
3. 81.4 ppm FAC, pH 4.9, with TEA.

Albumin concentrations used were:
1. 750 ppm
2. 1000 ppm
3. 1250 ppm

The results are presented in the following table:

TABLE 3

| Level of Albumin Addition Causing Incomplete Kill | | |
|---|---|---|
| | pH 4.9 | pH 7.0 |
| Escherichia coli | >1250 ppm | 1250 ppm |
| Pseudomonas aeruginosa | >1250 ppm | 1000 ppm |
| Staphylococcus aureus | 1250 ppm | 1000 ppm |

FAC = 72 ppm

The results indicate that at pH 5 it takes a higher level of organics than at pH 7 to reduce the active components to a point at which 100% kill of the organic is not obtained.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An antimicrobial solution, comprising:
   a first component comprising an effective amount of a hypochlorous acid solution, wherein the hypochlorous acid solution has a pH of about 4 to about 6, and wherein the hypochlorous acid solution comprises a buffer selected from the group consisting of a phosphate buffer, acetate buffer, citrate buffer, borate buffer, and combinations thereof; and
   a second component comprising a catalyst, which catalyzes the conversion of hypochlorous acid into dichlorine monoxide,
   wherein, when the first and second components are combined, the combination produces an activated solution comprising a therapeutically effective amount of dichlorine monoxide, and
   wherein the activated solution has a pH in a range of from about 4 to about 10.

2. The solution of claim 1, wherein the hypochlorous acid solution has a pH of from about 5.0 to about 6.0.

3. The solution of claim 1, wherein the catalyst is selected from the group consisting of a phosphate ion, chloride ion, tertiary amine, sodium hypochlorite, citric acid, and combinations thereof.

4. The solution of claim 1, wherein the catalyst is triethanolamine.

5. The solution of claim 4, wherein the triethanolamine is present in a concentration of about 0.3 ppm to about 1.5 ppm.

6. The solution of claim 1, wherein the activated solution has a pH of from about 5.0 to about 6.0.

7. The solution of claim 1, wherein the hypochlorous acid solution is contained within a first container, and the catalyst is contained within a second container.

8. A method for treating a wound or infection in a mammal, the method comprising:
adding to a solution comprising an effective amount of hypochlorous acid a catalyst, which catalyzes the conversion of hypochlorous acid into dichlorine monoxide, to produce an activated solution comprising a therapeutically effective amount of dichlorine monoxide; and
administering the activated solution to treat the wound or infection,
wherein the hypochlorous acid solution has a pH of about 4 to about 6,
wherein the activated solution has a pH in a range of from about 4 to about 10, and
wherein the hypochlorous acid solution further comprises a buffer selected from the group consisting of a phosphate buffer, acetate buffer, citrate buffer, borate buffer, and combinations thereof.

9. The method of claim 8, wherein the hypochlorous acid solution has a pH of from about 5.0 to about 6.0.

10. The method of claim 8, wherein the catalyst is selected from the group consisting of a phosphate ion, chloride ion, tertiary amine, sodium hypochlorite, citric acid, and combinations thereof.

11. The method of claim 8, wherein the catalyst is triethanolamine present in a concentration of about 0.3 ppm to about 1.5 ppm.

12. The method of claim 8, wherein the activated solution has a pH of from about 5.0 to about 6.0.

13. The method of claim 8, wherein the infection is caused by the bacteria *Pseudomonas aeruginosa, Escherichia coli, Enterococcus hirae, Acinetobacter baumannii, Acinetobacter* species, *Bacteroides fragilis, Enterobacter aerogenes, Enterococcus faecalis*, Vancomycin resistant-*Enterococcus faecium* (VRE, MDR), *Haemophilus influenzae, Klebsiella oxytoca, Klebsiella pneumoniae, Micrococcus luteus, Proteus mirabilis, Serratia marcescens, Staphylococcus aureus, Staphylococcus epidermidis, Staphylococcus haemolyticus, Staphylococcus hominis, Staphylococcus saprophyticus, Streptococcus pneumoniae, Streptococcus pyogenes, Salmonella choleraesuis, Shigella dysenteriae* or a combination thereof.

14. The method of claim 8, wherein the wound is an oral ulcer, skin ulcer, burn, peritonitis, periodontal disease, gingival disease or a combination thereof.

15. The method of claim 14, wherein the skin ulcer is a diabetic foot ulcer.

16. The method of claim 8, wherein the infection is a pulmonary, ophthalmic, otic, nasal or sinus infection.

17. The method of claim 16, wherein the pulmonary infection is in a human mammal afflicted with cystic fibrosis.

18. A method for disinfecting a surface, the method comprising:
adding to a solution comprising an effective amount of hypochlorous acid a catalyst, which catalyzes the conversion of hypochlorous acid into dichlorine monoxide, to produce an activated solution comprising a surface-disinfecting effective amount of dichlorine monoxide; and
contacting the surface with the activated solution to disinfect the surface, wherein the hypochlorous acid solution has a pH of about 4 to about 6,
wherein the activated solution has a pH in a range of from about 4 to about 10, and
wherein the hypochlorous acid solution further comprises a buffer selected from the group consisting of a phosphate buffer, acetate buffer, citrate buffer, borate buffer, and combinations thereof.

19. The method of claim 18, wherein the hypochlorous acid solution has a pH of from about 5.0 to about 6.0.

20. The method of claim 18, wherein the catalyst is selected from the group consisting of a phosphate ion, chloride ion, tertiary amine, sodium hypochlorite, citric acid, and combinations thereof.

21. The method of claim 18, wherein the catalyst is triethanolamine in a concentration of about 0.3 ppm to about 1.5 ppm.

22. The method of claim 18, wherein the surface is a plastic surface, metal surface, glass surface or a combination thereof.

23. The method of claim 18, wherein the surface is on an artificial heart valve, orthopedic appliance, implantable pacemaker, implantable tube, implantable stent, implantable mesh or a combination thereof.

24. The method of claim 23, wherein the surface is on a bronchoscope, colonoscope, sigmoidoscope, hysteroscope, laproscope, arthroscope, gastroscope or cystoscope.

25. The solution of claim 1, wherein the hypochlorous acid solution is prepared by electrolysis.

26. The solution of claim 1, wherein the hypochlorous acid solution is prepared by dissolving chlorine in a dilute aqueous alkali metal hydroxide solution.

27. The solution of claim 8, wherein the hypochlorous acid solution is prepared by electrolysis.

28. The solution of claim 8, wherein the hypochlorous acid solution is prepared by dissolving chlorine in a dilute aqueous alkali metal hydroxide solution.

29. The solution of claim 18, wherein the hypochlorous acid solution is prepared by electrolysis.

30. The solution of claim 18, wherein the hypochlorous acid solution is prepared by dissolving chlorine in a dilute aqueous alkali metal hydroxide solution.

* * * * *